(12) United States Patent
Stevenson et al.

(10) Patent No.: US 6,875,450 B2
(45) Date of Patent: Apr. 5, 2005

(54) COMESTIBLE FOR PREVENTING CALCIUM OXALATE UROLITHIASIS IN CANINE ANIMALS

(75) Inventors: Abigail Emma Stevenson, Melton Mowbray (GB); Brigitte Eshter Hope Smith, Leicestershire (GB); Peter John Markwell, Melton Mowbray (GB)

(73) Assignee: Mars Incorporated, McLean, VA (US)

( * ) Notice: Subject to any disclaimer, the term of this patent is extended or adjusted under 35 U.S.C. 154(b) by 0 days.

(21) Appl. No.: 10/169,318

(22) PCT Filed: Jan. 4, 2001

(86) PCT No.: PCT/GB01/00021

§ 371 (c)(1),
(2), (4) Date: Oct. 3, 2002

(87) PCT Pub. No.: WO01/49130

PCT Pub. Date: Jul. 12, 2001

(65) Prior Publication Data

US 2003/0143286 A1 Jul. 31, 2003

(30) Foreign Application Priority Data

Jan. 7, 2000 (GB) .............................................. 0000360

(51) Int. Cl.⁷ .......................... A23K 1/18; A23K 1/175; A61K 9/00; A01N 59/00; A23L 1/30
(52) U.S. Cl. ...................... 424/600; 424/400; 424/439; 424/601; 424/602; 426/74; 426/805
(58) Field of Search ................................ 424/400, 600, 424/439, 601, 602, 60; 426/74, 805, 2; 514/1

(56) References Cited

U.S. PATENT DOCUMENTS 6,133,317 A * 10/2000 Hart ............................ 514/574
6,156,355 A 12/2000 Shields, Jr. et al.

OTHER PUBLICATIONS

Stevenson, Abigail E., et al.; Effects of dietary potassium citrate supplementation on urine pH and urinary relative superstaturation of calcium oxalate and struvite in healthy dogs; AJVR, vol. 61, No. 4, Apr. 2000.

Bartges, Joseph W., et al.; Diet effect on activity product ratios of uric acid, sodium urate, and ammonium urate in urine formed by healthy Beagles; Am J Vet Res, vol. 56, No. 3, Mar. 1995.

Bartges, Joseph W., et al.; Influence of four diets on uric acid metabolism and endogenous acid production in healthy Beagles; AJVR, vol. 57, No. 3, Mar. 1996.

Lulich, Jody P., et al.; Epidemiology of Canine Calcium Oxalate Urolliths, Identifying Risk Factors; Veterinary Clinics of North America: Small Animal Practice, vol. 29, No. 1, Jan. 1999.

* cited by examiner

Primary Examiner—David M. Naff
Assistant Examiner—Deborah K. Ware
(74) Attorney, Agent, or Firm—Fulbright & Jaworski, LLP (57) ABSTRACT

The present invention provides comestibles and related aspects for use in maintaining canine urinary tract health. In particular the comestibles and related aspects are useful in preventing the initial occurrence of canine calcium oxalate urolithiasis. The present invention also provides a comestible, which when fed to a small breed canine animal results in a urine specific gravity of 1.025 or below, for use in preventing the initial occurrence of calcium oxalate urolithiasis in the canine animal and related aspects. The comestible includes the following ingredients in the ranges indicated, for use in preventing the initial occurrence of calcium oxalate urolithiasis in a canine animal and related aspects:

| Nutrient | g/400 kcal |
| --- | --- |
| Calcium | 0.65–1.3 |
| Phosphorus | 0.5–1.2 |
| Magnesium | from 0.04 |
| Potassium | from 0.5 |
| Sodium | 0.6–1.2. |

15 Claims, 5 Drawing Sheets

FIG. 1

RELATIONSHIP BETWEEN URINARY CALCIUM OXALATE RELATIVE SUPERSATURATION (RSS) AND CRYSTALLISATION BEHAVIOURS

FIG. 2a

MEAN TRIAL URINE pH OF EIGHT BEAGLES, MINIATURE SCHNAUZERS OR LABRADOR RETRIEVERS

FIG. 2b

MEAN DIURNAL URINE pH PROFILE OF EIGHT BEAGLES, MINIATURE SCHNAUZERS OR LABRADOR RETRIEVERS

FIG. 3

MEAN DAILY URINE VOLUME (ml/DAY) (A) AND MEAN DAILY URINE VOLUME (ml/kg $BWT^{0.75}$) (B) OF EIGHT BEAGLES, MINIATURE SCHNAUZERS AND LABRADOR RETRIEVERS

FIG. 4

MEAN NUMBER OF URINATIONS PER DAY OF EIGHT BEAGLES, MINIATURE SCHNAUZERS AND LABRADOR RETRIEVERS

FIG. 5

MEAN URINE SPECIFIC GRAVITY OF EIGHT BEAGLES, MINIATURE SCHAUZERS OR LABRADOR RETRIEVERS FED PEDEGREE ADVANCE ADULT SUPREME (DRY) (MBE, LA CHAPELLE)

FIG. 6

AVERAGE CALCIUM OXALATE RSS PRODUCED BY LABRADOR RETRIEVERS AND MINIATURE SCHNAUZERS ON 8% AND 75% DIETARY MOISTURE

FIG. 7

AVERAGE DAILY URINE SPECIFIC GRAVITY PRODUCED BY LABRADOR RETRIEVERS AND MINIATURE SCHNAUZERS ON 8% AND 75% DIETARY MOISTURE

FIG. 8

AVERAGE CALCIUM OXALATE RSS PRODUCED BY LABRADOR RETRIEVERS AND MINIATURE SCHNAUZERS ON 0.2 AND 1.2g SODIUM / 400 kcal

FIG. 9

AVERAGE DAILY URINE SPECIFIC GRAVITY PRODUCED BY LABRADOR RETRIEVERS AND MINIATURE SCHNAUZERS ON 0.2 AND 1.2g SODIUM / 400 kcal

US 6,875,450 B2

COMESTIBLE FOR PREVENTING CALCIUM OXALATE UROLITHIASIS IN CANINE ANIMALS

This application is a National Stage application of International Application No. PCT/GB01/00021 filed Jan. 4, 2001, which claims priority to Great Britain Application No. 0000360.8 filed Jan. 7, 2000.

FIELD OF THE INVENTION

The present invention provides comestibles and related aspects for use in maintaining canine urinary tract health. In particular the comestibles and related aspects are useful in preventing the initial occurrence of canine calcium oxalate urolithiasis.

BACKGROUND OF THE INVENTION

Urolithiasis can be defined as the presence of macroscopic mineralisation within the urinary tract, ranging in size from sand particles to radiographically obvious uroliths. Uroliths of a variety of different mineral types have been identified within the canine and feline lower urinary tract, such as struvite, calcium oxalate, calcium phosphate, uric acid and urates.

Lower urinary tract diseases associated with mineral precipitation are important clinical problems in dogs and cats. Whilst a number of different minerals may be present in the lower urinary tract, two are of particular importance; (a) struvite (magnesium ammonium phosphate) and (b) calcium oxalate. Precipitation of these minerals may be associated with disease in animals such as dogs, cats and humans when it results in urolithiasis.

Urolithiasis continues to be an important clinical problem in dogs. Struvite (magnesium ammonium phosphate) has been the most numerically important type of urolith found in dogs. Recent data suggest that the number of calcium oxalate uroliths is increasing in dogs, and that uroliths of this type may now be of equal or greater importance than struvite, particularly in certain breeds. The majority of dogs with struvite urolithiasis have an associated urinary tract infection with urease-producing bacteria, such as staphylococci or *Proteus spp.* Hydrolysis of urea by the enzyme urease, ultimately results in the formation of ammonia and carbonate which creates an increasingly alkaline environment in the urine. These conditions are ideal for the development of struvite uroliths, but also favour the formation of a number of other urolith types including calcium carbonate and apatite. Thus, in the majority of dogs with struvite urolithiasis appropriate anti-microbial agents form an essential part of therapy. Usually, once the urinary tract infection has been fully eradicated, the dog will not require any long term dietary management. Nevertheless, a number of canine diets designed as a nutritional aid for dogs which suffer from struvite urolithiasis (such as Hills canine s/d) are on the market. Most pet food diets which are designed as nutritional aids for pets with struvite urolithiasis are contraindicated for use with pets suffering from non-struvite urolithiasis.

Cases of calcium oxalate urolithiasis require surgical removal. Only then are dietary measures adopted to prevent reformation of the urolith. Clearly, it would be advantageous to provide a comestible which is designed for management or prevention of calcium oxalate uroliths, avoiding their initial formation in canine animals.

SUMMARY OF THE INVENTION

The present invention provides such a desired comestible together with other related aspects for use in maintaining canine urinary tract health, in particular in individual canine animals which have not been recognised as suffering from calcium oxalate urolithiasis.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

According to a first aspect of the invention, there is provided a comestible comprising the following ingredients in the ranges indicated, for use in preventing the initial occurrence of calcium oxalate urolithiasis in a canine animal.

| Nutrient | g/400 kcal |
| --- | --- |
| Calcium | 0.65–1.3 |
| Phosphorus | 0.5–1.2 |
| Magnesium | from 0.04 |
| Potassium | from 0.5 |
| Sodium | 0.6–1.2 |

Preferred levels of the above nutrients are:

| Nutrient | g/400 kcal |
|---|---|
| Calcium | 0.85–1.0 |
| Phosphorus | 0.75–0.9 |
| Magnesium | from 0.1 |
| Potassium | from 0.8 |
| Sodium | from 0.8 |

The comestible according to the first aspect of the invention may, when fed to a canine animal, result in a urine specific gravity of 1.025 or below.

According to a second aspect of the present invention there is provided a comestible which when fed to a small breed canine animal results in a urine specific gravity of 1.025 or below, for use in preventing the initial occurrence of calcium oxalate urolithiasis in said canine animal.

Urine specific gravity is a straightforward measurement to make. A urine sample is taken (preferably fresh, within 30 minutes of voiding). A refractometer or specific gravity (SG) meter (available from Analytical Supplies Ltd., Derby, UK) is used to give a measure of specific gravity. The meter used should be calibrated to read within the range 1.000 to 1.060.

In this text, references to concentrations per kcal are to kcal of total metabolisable energy intake.

The term comestible includes a diet or foodstuff, usually a pet food product suitable for administration to a canine animal. It includes the ingredients formulated as a commercial product, including those suitable for sale over the counter in supermarkets, as well as medicament or pharmaceutical composition. The nutrient concentration used herein means the usual available (for digestion) form of the nutrient.

In the present text, the term "canine" or "canine animal" means all animals falling within the mammalian family Canidae, such as dogs, wolves and foxes, in particular "domestic" dogs (*Canis domesticus*).

The first and second aspects of the invention provide a comestible for use in preventing the initial occurrence of calcium oxalate urolithiasis in a canine animal. The comestible achieves this use by minimising the risk of calcium oxalate formation. In particular, an advantage of the present invention is the diet or foodstuff for use in minimising the risk of calcium oxalate formation in healthy dogs; that is dogs which have not previously been known to suffer from calcium oxalate uroliths. Accordingly, the comestible according to the first and second aspects of the invention can be used as a prophylactic measure for all canine animals, including healthy ones. In this text, the term "prevention" includes the prevention and reduction of calcium oxalate formation.

There are a number of known predisposing factors for calcium oxalate formation:
1. Sex—calcium oxalate uroliths occur more frequently in males, possibly due to anatomical differences between male and female dogs: the shorter, wider urethra of the female may make it easier to pass small stones that could be trapped in males.
2. Age—calcium oxalate uroliths form more commonly in the older dog. The older dog is considered to be of five years or more.
3. Breed—from the literature it is apparent that small breed dogs form calcium oxalate uroliths far more commonly than larger breeds.

Small breeds (<15 kg body weight) make up around 65% of the Japanese dog population and 43% of the UK dog population; they also represented 28% of new registrations in one month in the USA. Thus, diets designed to promote urinary tract health, based around reducing the risk of initial calcium oxalate formation in particular for this group of dogs, would be recognised, in the art, as providing a solution to a problem. Small breed dogs include Yorkshire terrier, Miniature Schnauzer, Lhasa Apso, Miniature Poodle, Shih tzu, other poodle, Bichon Frise, Pomeranian, Chihuahua, Maltese terrier, Cairn terrier, Pekingese, Dachshund, Papillon, Cavalier King Charles Spaniel, West Highland White terrier, Tibetan Terrier, Scottish Terrier, Shetland Sheepdog, Jack Russell Terrier and Corgi. The present invention is particularly preferred for use with small breed dogs.

There is evidence that the number of calcium oxalate uroliths may now be increasing in comparison to struvite. There are a number of possible explanations for this trend, including:
  Faster and more effective treatment of urinary tract infections that may otherwise lead to struvite formation
  More successful in vivo dissolution of struvite uroliths (thus they are not submitted for analysis)
  Dogs are living longer than they used to, and calcium oxalate formation tends to occur in more senior dogs
  Smaller dogs having a longer life-span, calcium oxalate is more likely in older dogs.

Figure 1:
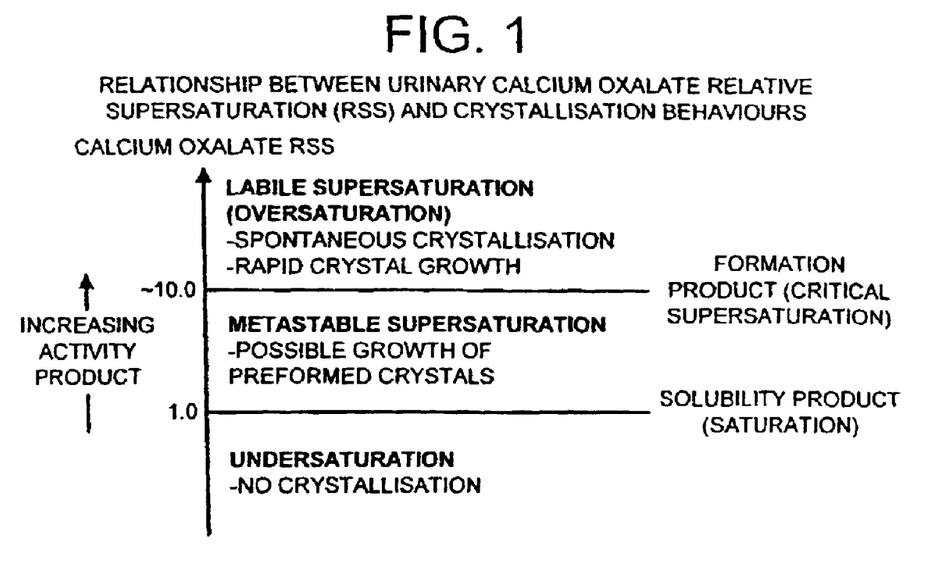
FIG. 1 is an illustration of the relationship between urinary calcium oxalate relative to supersaturation and crystallisation behavours.

The inventors of the present invention have developed a technique to measure the effect of diet on calcium oxalate saturation levels in the urine called urinary RSS (Relative Super Saturation). A description of RSS measurement is set out in Markwell, P. J., Smith, B. H. E., and McCarthy K. P., Animal Technology (1999), Vol. 50, No. 2, pages 61 to 66. Diets promoting production of urine undersaturated with calcium oxalate (RSS<1.0), (FIG. 1) will prevent recurrence of calcium oxalate formation. The formation product of calcium oxalate is estimated to be approximately 10 times the solubility product. This is equivalent to a RSS of approximately 10. Urine with a calcium oxalate RSS of between 1 and 10 may thus be considered to be in a state of metastable supersaturation and homogenous crystallisation would not be expected to occur; heterogeneous crystallisation is also unlikely within the lower region of the metastable zone of supersaturation (<5.0).

Urine with an RSS within this zone would be considered appropriate for promoting urinary tract health, as it should minimise the risk of calcium oxalate formation, even in healthy animals. The invention results in production of urine with a low calcium oxalate relative supersaturation (RSS<5).

The diets and foodstuffs according to this invention are suitable for maintenance of all dogs, including adult dogs, and can advantageously be fed to normal healthy dogs to minimise the risk of calcium oxalate urolithiasis.

In accordance with the first and second aspects of the invention, the comestible preferably does not contain high levels of dietary oxalate. The level is preferably less than 60 mg/400 kcal, more preferably less than 50 mg/400 kcal and even more preferably, less than 40 mg/400 kcal. Most preferably, it is less than 30 mg/400 kcal.

A preferred feature of the comestible according to the present invention is that it provides from 16 g/400 kcal protein. Such protein levels allow for the feeding of a canine animal indefinitely without suffering from problems associated with low protein levels (such as impaired renal function). Preferred protein levels are 20 g/400 kcal or above, 25 g/400 kcal or above, up to 50 g/400 kcal.

Previous canine diets designed to be used for dogs with oxalate urolithiasis have been based on the premise that all nutrients should be restricted as low as possible. Such diets are not appropriate for long-term use. The present invention overcomes this problem in the art. Without limiting the present invention to the comments below on particular nutrients, some key points have been recognised as follows:

Dietary Calcium

Known diets with a higher calcium (and phosphorus) content, particularly when linked with lower sodium content and/or higher urine pH, tended to result in production of urine with higher calcium oxalate RSS. A relationship between dietary calcium content, urinary calcium concentration and calcium oxalate RSS has also been observed in-house by the applicant company in dogs. Thus the maximum dietary calcium level is restricted when compared to normal adult maintenance specifications.

Recommended dietary calcium: 0.65–1.3 g/400 kcal.

Dietary Phosphorus

Since the diet or foodstuff concentrates on reducing the risk of calcium oxalate the recommended range for dietary phosphorus is determined primarily by the recommendations for calcium and the impact of phosphorus levels on the Ca:P ratio. Dietary phosphorus is important to control in the specification because of the link between dietary phosphorus and the progression of chronic renal failure (a common condition in dogs).

Recommended dietary phosphorus: 0.5–1.2 g/400 kcal.

Calcium and phosphorus are closely nutritionally interrelated and the Ca:P ratio in a diet will influence the absorption and uptake of each mineral from the gastrointestinal tract. The greater the Ca:P ratio, the more likely the diet is to produce an alkaline urine. Conversely, the smaller the ratio of Ca:P, the more likely the diet is to produce an acidic urine. A preferred Ca:P ratio is 0.8–1.4, more preferably 0.8–1.2, even more preferably 1.0.

Dietary Magnesium

There are no additional restrictions for magnesium other than those for adult maintenance. It has been suggested in the art that magnesium may be a moderately effective inhibitor of calcium oxalate crystallisation, through its ability to form complexes with oxalate in urine. However, in a trial conducted in-house by the applicant company, supplementing a dry diet with up to 0.17 g dietary magnesium/400 kcal, calcium oxalate RSS remained unchanged. Recommended dietary magnesium: minimum 38.4 mg/400 kcal (adult maintenance specification, WCPN minimum nutrient requirements, BSAVA Manual of Companion Animal Nutrition and Feeding, Ed. N. Kelly and J. Wills, 1996, page 254, Appendix 1).

Dietary Potassium

Because cats tend to excrete more potassium when receiving urine acidifying diets, the minimum potassium level was increased for diets designed to promote urinary tract health. This condition does not appear to occur in dogs (noted by the applicant company) and thus there are no additional specifications for potassium other than those for adult maintenance.

Recommended dietary potassium: minimum 0.5 g/400 kcal (adult maintenance specification, WCPN minimum nutrient requirements, BSAVA Manual of Companion Animal Nutrition and Feeding, Ed. N. Kelly and J. Wills, 1996, page 254, Appendix 1).

Dietary Sodium

Low urine volume has long been recognised as a risk factor for urolithiasis in people and other species. A study conducted in-house, supplementing a semi-moist dog food (20.9% moisture) with 0.46 g, 0.63 g and 1.08 g sodium/400 kcal demonstrated a stepwise increase in water intake as dietary sodium increased, although the effect varied markedly between individual dogs. This may lead to the production of a more dilute urine that would be expected, for a given solute load, to have a lower calcium oxalate RSS. However, this is a controversial area. It has been suggested that increased dietary sodium may lead to increased urinary calcium excretion. However, this effect has not been shown in other published work, and additionally a study in-house in which dogs were supplemented with sodium (as sodium chloride) at levels up to 1.6 g/400 kcal did not demonstrate any increase in calcium excretion. Therefore, the minimum sodium recommendation has been increased when compared to adult maintenance specifications.

Although the maximum for sodium in senior dogs was reduced to 0.7 g/400 kcal in 1991 WCPN minimum nutrient requirements, BSAVA Manual of Companion Animal Nutrition and Feeding, Ed. N. Kelly and J. Wills, 1996, page 254, Appendix 1, due to the possible link between hypertension and high sodium intake, particularly in stressed dogs, the potential benefits of increasing dietary sodium and thus water turnover outweigh the slight risk of hypertension in small breed senior dogs.

Recommended dietary sodium: 0.5–1.2/400 kcal.

Preferably, the comestible according to the first and second aspects of the present invention are a commercial petfood product or a commercial dietary supplement. The comestible may be a dry, semi-dry, moist or a liquid (drink) product. Moist products include food which has a moisture content of 70 to 90%. This form of product is usually sold in tins or foil containers. Dry products include food which have a similar composition, but with 5 to 15% moisture and presented as biscuit-like kibbles.

The comestible according to the present invention which is a dietary supplement, provides to the canine animal in addition to other nutrient intake, a total intake of the following ingredients in the ranges indicated.

| Nutrient | g/400 kcal |
| --- | --- |
| Calcium | 0.65–1.3 |
| Phosphorus | 0.5–1.2 |

-continued

| Nutrient | g/400 kcal |
|---|---|
| Magnesium | from 0.04 |
| Potassium | from 0.5 |
| Sodium | 0.6–1.2 |

Alternatively, the dietary supplement provides, in addition to other nutrient intake of a canine animal, a total diet which results in the small breed canine animal having a urine specific gravity of 1.025 or below, for use in preventing the initial occurrence of calcium oxalate urolithiasis in the animal.

Preferred features of the first and second aspects of the invention as described herein also apply to the dietary supplement.

The comestible according to the present invention encompasses any product which a canine animal may consume in its diet. Thus, the invention covers standard food products, as well as pet food snacks (for example snack bars, biscuits and sweet products). The comestible is preferably a cooked product. It may incorporate meat or animal derived material (such as beef, chicken, turkey, lamb, blood plasma, marrowbone etc, or two or more thereof). The comestible alternatively may be meat free (preferably including a meat substitute such as soya, maize gluten or a soya product) in order to provide a protein source. The product may contain additional protein sources such as soya protein concentrate, milk proteins, gluten etc. The product may also contain a starch source such as one or more grains (e.g. wheat, corn, rice, oats, barley etc) or may be starch free. The product may be provided as a gelatinised cereal product, such as a gelatinised starch matrix. A typical dry commercial dog food contains about 30% crude protein, about 10–20% fat and the remainder being carbohydrate, including dietary fibre and ash. A typical wet, or moist product contains (on a dry matter basis) about 40% fat, 50% protein and the remainder being fibre and ash. The present invention is particularly relevant for a comestible which is a diet, foodstuff or supplement as herein described which is sold as a diet, foodstuff or supplement for a dog.

The comestible is preferably packaged. In this way the consumer is able to identify, from the packaging, the ingredients in the comestible and identify that it is suitable for the canine animal in question. The packaging may be metal (usually in the form of a tin or flexifoil), plastic, paper or card. The amount of moisture in any product may influence the type of packaging which can be used or is required.

Where the invention comprises a "total" comestible (including a total diet or animal foodstuff) it is recommended that all dietary requirements as set out in 'Association of American Feed Control Officials', official publication 1996, page 374, are also met by the total comestible. This should include the recommended levels of fibre, carbohydrate, energy levels etc. These complete comestibles may include: maize gluten, rice, wheat, meat and meat derivatives, fish and fish derivatives, sugar beet fibre, other fibre, such as chicory fibre or coconut endosperm fibre, minerals, vitamins, dairy products, taurine and water.

When the invention is a dietary supplement the recommended levels set out in the 'Association of American Feed Control Officials' may or may not be met by the supplement. The dietary supplement may be provided by a foodstuff, tablet, powder or liquid formulation preferably, but not exclusively for oral consumption or administration.

A third aspect of the invention provides a method of preventing the initial occurrence of calcium oxalate urolithiasis in a canine animal, comprising feeding to said canine animal a comestible comprising the following ingredients in the ranges indicated:

| Nutrient | g/400 kcal |
|---|---|
| Calcium | 0.65–1.3 |
| Phosphorus | 0.5–1.2 |
| Magnesium | from 0.04 |
| Potassium | from 0.5 |
| Sodium | 0.6–1.2 |

A fourth aspect of the present invention provides a method of preventing the initial occurrence of calcium oxalate urolithiasis in a small breed canine animal comprising feeding to said canine animal a comestible which provides the animal with a urine specific gravity of 1.025 or below.

Preferred features of the first and second aspects of the invention also apply to the third and fourth aspects. The comestible may include levels of protein which enable long term feeding of the product without the development of protein depletion. Protein levels are preferably from 16 g/400 kcal nutrient intake, more preferably from 20 g/400 kcal nutrient intake. Canned diets have preferred protein levels of around 25 g/400 kcal up to around 50 g/400 kcal.

The method may be used for an indefinite period of time, for example, periods from weeks to periods of years.

A fifth aspect of the invention provides the use of a comestible in preventing the initial occurrence of calcium oxalate urolithiasis in a canine animal, wherein the comestible comprises the following ingredients in the ranges:

| Nutrient | g/400 kcal |
|---|---|
| Calcium | 0.65–1.3 |
| Phosphorus | 0.5–1.2 |
| Magnesium | from 0.04 |
| Potassium | from 0.5 |
| Sodium | 0.6–1.2 |

A sixth aspect of the present invention provides the use of a comestible, which when fed to a small breed canine animal results in a urine specific gravity of 1.025 or below in preventing the initial occurrence of calcium oxalate urolithiasis in said canine animal.

All preferred features of aspects one to four also apply to the fifth and sixth aspects.

A seventh aspect of the invention provides the use of the following ingredients in the ranges indicated:

| Nutrient | g/400 kcal |
|---|---|
| Calcium | 0.65–1.3 |
| Phosphorus | 0.5–1.2 |
| Magnesium | from 0.04 |
| Potassium | from 0.5 |
| Sodium | 0.6–1.2 | in the manufacture of a product for use in preventing the initial occurrence of calcium oxalate urolithiasis in a canine animal.

An eighth aspect of the present invention provides the use of ingredients in the manufacture of a product, which when fed to a small breed canine animal results in urine specific gravity of 1.025 or below for preventing the initial occurrence of calcium oxalate urolithiasis in a canine animal.

Preferred features of aspects one to six also apply to the seventh or eighth.

A ninth aspect of the invention provides a process for the preparation of a comestible according to any one of the first, second, seventh or eighth aspects of the invention.

The process comprises mixing together the ingredients, optionally heating to cook any raw ingredients and presenting the mixture into a form suitable for consumption or administration to an animal. This may include extruding the mix from the mixing container and coating the extruded mix with spray, such as digest spray.

The present invention will now be described with reference to the following non-limiting examples;

EXAMPLES

Example 1

An investigation as to possible differences in urine composition between small and non-small canine breeds.

Do Miniature Schnauzers produce urine of different composition to that of Labrador Retrievers and Beagles, when fed the same dry diet?

A trial was conducted examining the differences in urine pH, urine volume and specific gravity, number of urinations per day, urinary relative supersaturations and excretion of urine analytes between Labrador Retrievers (LR), Miniature Schnauzers (MS) and Beagles (B). As previously mentioned, the MS is a breed identified as being predisposed to calcium oxalate formation.

Eight dogs of each breed were fed a standard commercial dry dog food for three weeks. The various nutrient profiles for calcium, phosphorus, magnesium, potassium and sodium for this dry dog food is as follows:

| Nutrient | g/400 kcal |
|---|---|
| Calcium | 1.52 |
| Phosphorus | 1.22 |
| Magnesium | 0.12 |
| Potassium | 0.79 |
| Sodium | 0.26 |
| Protein | 28.48 |
| Moisture | 7.33 |
| Fat | 17.74 |

-continued

| Nutrient | g/400 kcal |
|---|---|
| Ash | 8.61 |
| Nitrogen Free Extract | 44.10 |

Each individual urination was collected from each dog immediately after it was voided for two days in every four. The time of the urination, urine pH, urine volume and specific gravity were immediately recorded. The sample was then titrated to pH 2 and frozen for future measurement of relative supersaturation.

Figure 2A:
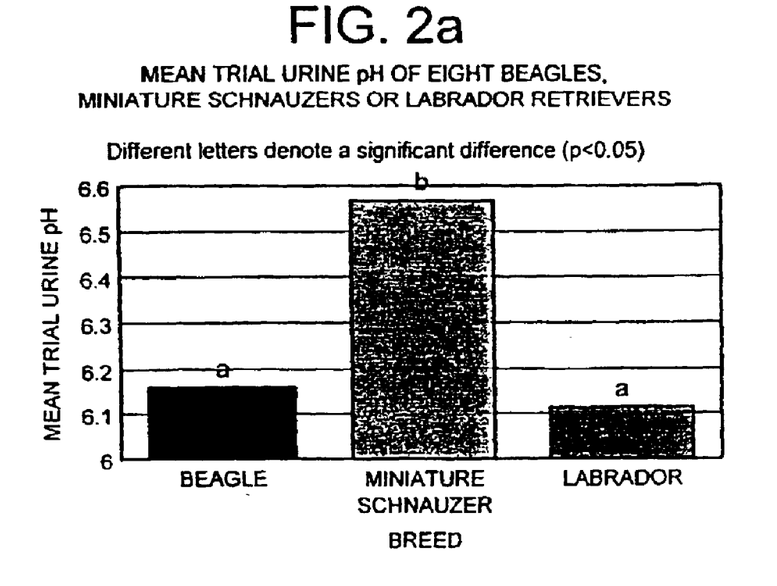
FIG. 2a is a graph showing the mean trial urine pH of certain dogs.
Figure 2B:
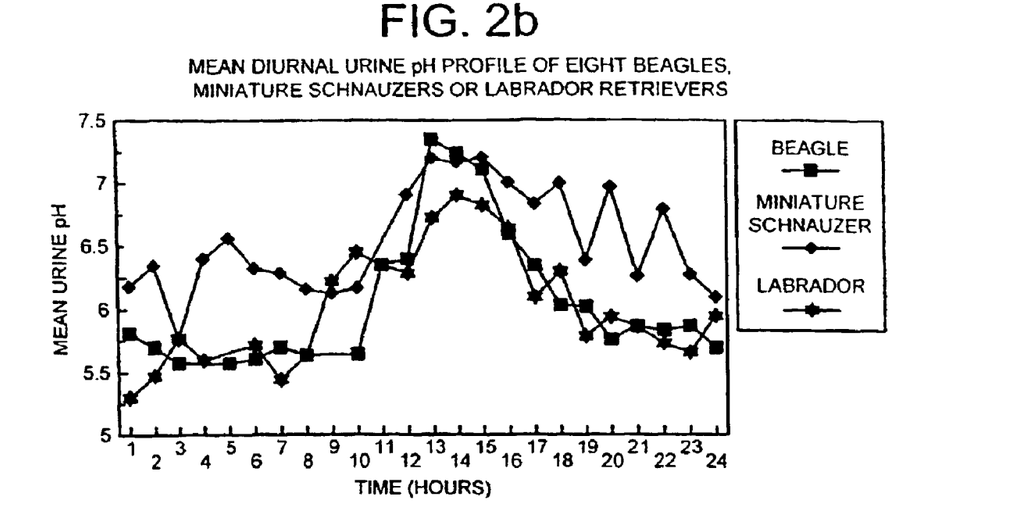
FIG. 2b is a chart showing the mean diurnal urine pH profile of certain dogs.

The results obtained, to date, show that the MS were significantly different from the LR and B in a numbers of ways (Table 1):

Urine pH (FIGS. 2a and 2b)

The MS produced urine with a significantly higher ($p<0.05$) pH than the LR or B. The LR and B were not significantly different from each other. When the urine pH was examined more closely as a 24 hour profile, all three breeds showed a post-prandial rise in urine pH. However, during the early morning and evening the MS maintained a higher urine pH than the LR and B.

Figure 3:
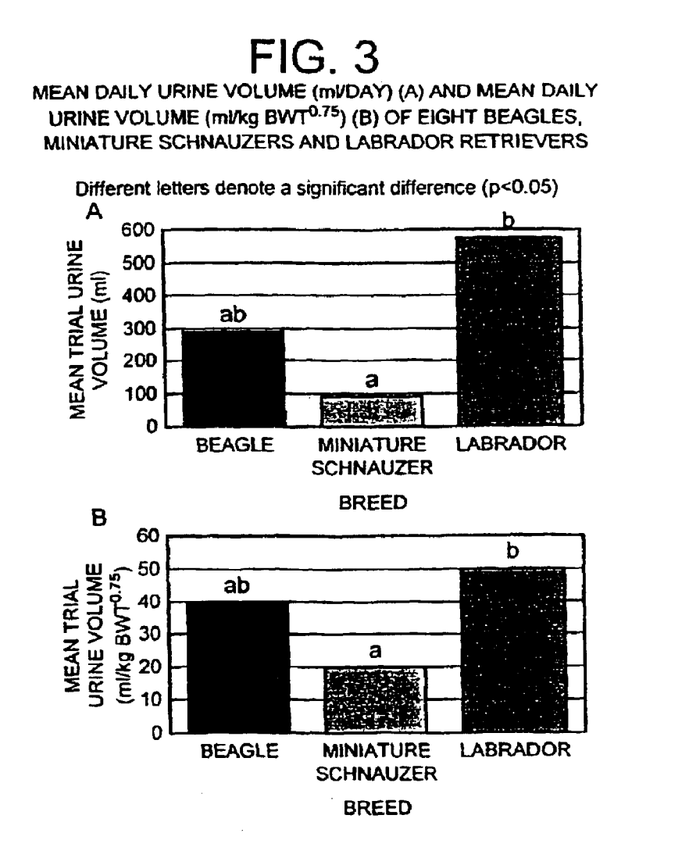
FIG. 3 is a graph showing the mean daily urine volume (ml/day) (A) and mean daily urine volume (ml/kg $BWT^{0.75}$) (B) of certain dogs.

Urine Volume (FIG. 3)

As expected, the LR produced the highest daily urine volume (significantly greater than the MS), due to differences in size. When metabolic bodyweight was taken into account, however, urine volume of the MS was still significantly ($p<0.05$) less than that of the LR.

Figure 4:
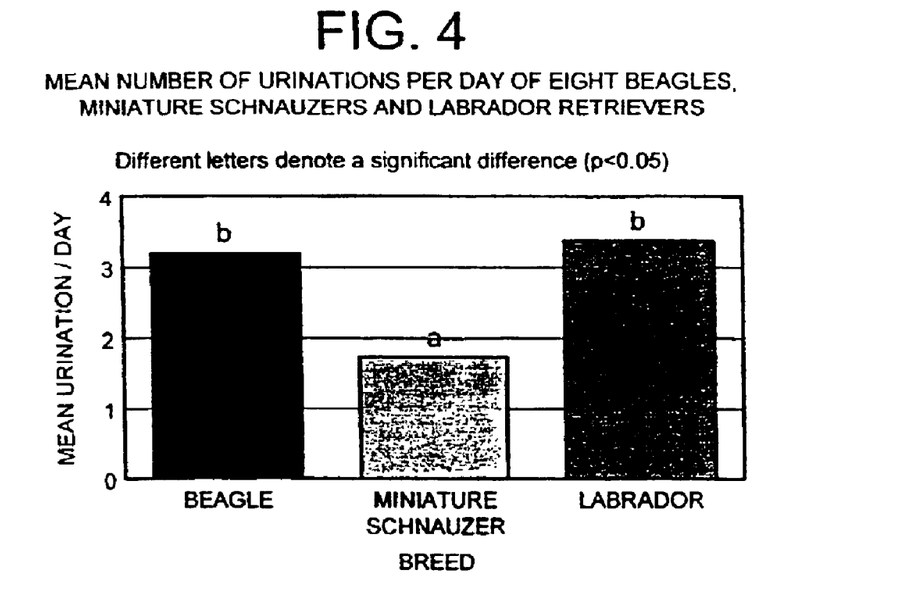
FIG. 4 is a graph showing the mean number of uninations per day of certain dogs.

Number of Urinations per Day (FIG. 4)

The LR and Beagles urinated significantly ($p<0.05$) more times per day than the MS.

Figure 5:
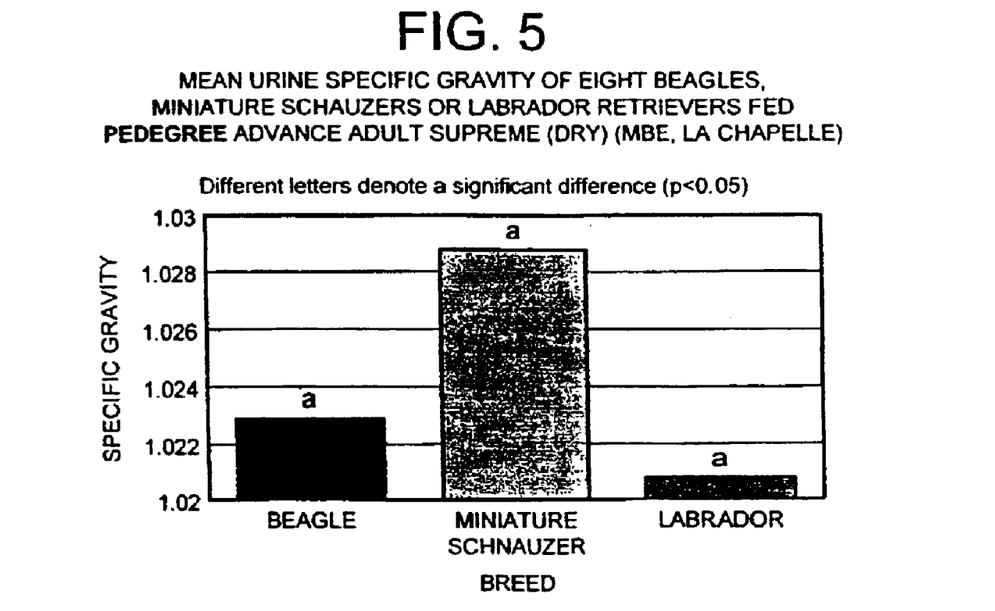
FIG. 5 is a graph showing the mean urine specific gravity of certain dogs fed Pedegree Advance Adult Supreme.

Urine Specific Gravity (FIG. 5)

The MS produced urine with the highest specific gravity (FIG. 5a), however, the differences between breeds were not significant ($p=0.22$). When examining the 24 hour profile, urine specific gravity tended to be higher in the early morning and evening than during the middle of the day. The MS showed a higher degree of variability during the early morning hours than the other breeds.

The differences between the breeds are summarised below.

TABLE 1

Summary of differences in urine parameters of the eight Miniature Schnauzers (MS), Beagles (B) and Labrador Retrievers (LR)

| Parameter | Differences |
|---|---|
| Urine pH | MS > B & LR |
| Urine volume (ml) | MS < LR |
| Urine volume (ml/kg body weight $^{0.75}$) | MS < LR |
| Number of urinations per day | MS < B & LR |
| Urine specific gravity | NS |

< or > denotes significant ($p < 0.05$) difference
NS denotes no significant difference

Example 2

Do Cairn Terriers (CT) produce urine of a different composition to that of Labrador Retrievers, when fed the same dry diet?

The data described in Example 1 provides a rationale for adult maintenance/senior dog diets designed to reduce the risk of calcium oxalate formation in healthy small dogs. However, to ensure that the increased risk of calcium oxalate urolithiasis applies to small dogs in general, a second breed of small dog, the Cairn terrier (CT) was screened. In the second trial, differences in urine pH, urine volume and specific gravity, number of urinations per day, urine relative supersaturations and excretion of urine analytes between Labrador Retrievers (LR) and Cairn Terriers were examined.

15 healthy dogs consisting of 8 LR (3 entire females, 1 neutered male and 4 neutered females; mean age 2.5±0.2 years) and 7 CT (5 neutered females, 2 neutered males; mean age 7.0±1.7 years) were fed a standard commercial dry Dog food once daily for 21 days. The various nutrient profiles for this dog food are shown in Table 2a:

Food allowances were calculated according to adult maintenance energy requirements (110 W (bodyweight expressed in kilograms)$^{0.75}$ kcal per day, see Berger I., Waltham Focus 1995, Volume 5, Issue 3, page 32) and adjusted during the study to ensure body weight maintenance within ±5% of original weight. Daily food intake and faeces quality were recorded throughout the trial. Water was provided ad libitum.

Dogs were housed in metabolism pens for two days in every four throughout the trial. During the remaining days the dogs were housed in pairs. During this time all dogs were walked once daily for approximately 15 minutes and group-exercised in grass paddocks for 1–2 hours.

While the dogs were in the metabolism pens, urine was collected from each dog and urine pH, volume and specific gravity were measured once daily using the non-invasive urine pH measuring system described in Stevenson et al; J. Nur. 128: 2761S–2762S (1998).

A urine collection was made during the last week of each diet phase, and frozen immediately after voiding for 48 hours, then defrosted and titrated to pH 2. Each sample was then analysed by HPLC to determine the concentrations of uric acid, creatinine, chloride, sulphate, phosphate, oxalate, citrate, pyrophosphate, ammonium, calcium, potassium, sodium and magnesium. The concentration of these analytes were entered into the Equil (Werness et al 1985., and Journal of Urology 134 1242–1244: Equil 2—a basic computer program to calculate urinary saturation) computer programme to determine the urinary relative supersaturation (activity product/solubility product) of each sample with respect to struvite, calcium oxalate and brushite.

Data were compiled into means (±standard deviation). Breeds were compared using unpaired t-tests. The level of significance was taken as p<0.05.

The results obtained show that the CT were significantly different from the LR in a number of ways (Table 2):

The CT produced urine with a significantly lower volume (ml/kg body weight/day; Table 2). They also tended to produce urine with a higher specific gravity although there was not a significant difference between breeds (Table 2). Urine pH was unaffected by breed (Table 2).

No significant differences in urinary concentrations of ammonium, phosphate, magnesium, or oxalate were detected between breeds). Urinary calcium concentration was significantly higher in the urine produced by the CT (P=0.0000001) than in that produced by the LR (Table 2).

The CT produced urine with a significantly higher CaOx and brushite RSS (Table 2). Struvite RSS was unaffected by breed (Table 2).

This diet was not designed to promote urinary tract health, and thus when compared with the nutrient specification for promoting urinary tract health in small dogs (Table 2a) this batch of commercial dog food was high in calcium, phosphorus and oxalate, and low in sodium.

Results from this study, including lower urine volume and higher calcium oxalate and brushite RSS indicate that healthy CT are at increased risk of calcium oxalate formation when compared to LR fed the same batch of diet.

This study also indicates the increased risk of calcium oxalate formation may apply to all small dog breeds, rather than specifically to MS.

TABLE 2

A comparison of urinary and blood parameters produced by Labrador retrievers and Cairn Terriers:

| Parameter | Labrador retrievers | Cairn terriers |
| --- | --- | --- |
| Calcium oxalate RSS | 6.55 ± 4.35$^a$ | 21.52 ± 2.52$^b$ |
| Brushite RSS | 0.38 ± 0.31$^a$ | 1.06 ± 0.46$^b$ |
| Struvite RSS | 0.51 ± 0.71 | 0.27 ± 0.23 |
| Urine pH | 5.90 ± 0.28 | 5.84 + 0.28 |
| Urinary calcium (mmol/l) | 0.54 ± 0.24$^a$ | 2.06 ± 0.46$^b$ |
| Urinary oxalate (mmol/l) | 1.34 ± 0.99 | 1.54 ± 0.42 |
| Urine volume (ml/kg BWT / d) | 24 ± 11$^b$ | 13 ± 5$^a$ |
| Urine specific gravity | 1.026 ± 0.017 | 1.028 ± 0.010 |

Different superscript letters within a row indicate a significant difference (P<0.05)

TABLE 2a

Dietary analysis Commercial dog food (Pedigree Advance Adult)

| NUTRIENT | UNIT | Nutrient Content 'AS IS' | Nutrient Content Per 400 kcal |
| --- | --- | --- | --- |
| Moisture | g | 6.50 | 7.15 |
| Protein | g | 26.50 | 29.15 |
| Fat | g | 14.70 | 16.17 |
| Ash | g | 8.70 | 9.57 |
| Nitrogen free extract | g | 43.60 | 47.96 |
| Predicted metabolisable energy | Kcal | 363.65 | |
| MINERALS | | | |
| Calcium | g | 1.54 | 1.69 |
| Phosphorus | g | 1.39 | 1.53 |
| Ca:P | | 1.11 | 1.11 |
| Sodium | g | 0.32 | 0.35 |
| Potassium | g | 0.67 | 0.74 |
| Magnesium | g | 0.10 | 0.11 |
| Iron | mg | 24.40 | 26.84 |
| Copper | mg | 2.11 | 2.32 |
| Manganese | mg | 8.66 | 9.53 |
| Zinc | mg | 21.90 | 24.09 |
| Oxalate | mg | 30.40 | 33.44 |

Example 3

Canine urinary pH and RSS screening trials to determine performance in terms of urine specific gravity urine pH, RSS and nutrient profile.

A number of canine urine specific gravity, canine urinary pH and RSS screening trials were conducted to determine whether a specific nutrient profile could be designed for a diet for use in maintaining urinary tract health, in particular reducing the risk of calcium oxalate formation.

The results are shown in the following tables (3 & 4). All trials were conducted in mixed breed panels (Labrador Retrievers, Beagles and Miniature Schnauzers) of normal healthy adult dogs.

TABLE 3

DRY DIETS

| | Urinary relative supersaturation | | Nutrients (/ 400 kcal) | | | | | |
|---|---|---|---|---|---|---|---|---|
| Trial No | Calcium Oxalate | Urine Specific Gravity | Calcium (g) | Phosphorus (g) | Magnesium (g) | Potassium (g) | Sodium (g) | Protein (g) |
| 1 | 1.03 ± 0.85$^a$ | — | 0.88 | 0.7 | 0.11 | 0.75 | 0.58 | 29.27 |
| 2 | 7.31 ± 6.60$^c$ | — | 1.57 | 1.22 | 0.11 | 0.7 | 0.25 | 31.87 |
| 3 | 3.84 ± 1.62$^{abc}$ | 1.033 ± 0.009 | 1.29 | 1.02 | 0.07 | 0.51 | 0.67 | 34.16 |
| 4 | 5.92 ± 2.59$^{bc}$ | 1.025 ± 0.012 | 1.78 | 1.19 | 0.1 | 0.76 | 0.2 | 28.27 |
| 5 | 2.84 ± 1.63$^{ab}$ | 1.022 ± 0.010 | 0.85 | 0.73 | 0.1 | 1.1 | 1.27 | 16.87 |
| 6 | 6.44 ± 2.63 | 1.021 ± 0.012 | 0.76 | 0.6 | 0.09 | 0.82 | 0.19 | 18.12 |

TABLE 4

WET DIETS

| | Urinary relative supersaturation | | Nutrients (/ 400 kcal) | | | | | |
|---|---|---|---|---|---|---|---|---|
| Trial No | Calcium oxalate | Urine Specific Gravity | Calcium (g) | Phosphorus (g) | Magnesium (g) | Potassium (g) | Sodium (g) | Protein (g) |
| 7 | 5.28 ± 2.56$^b$ | | 0.45 | 0.42 | 0.06 | 0.42 | 0.16 | 20.78 |
| 8 | 0.71 ± 0.36$^a$ | | 0.82 | 0.81 | 0.08 | 0.58 | 1.47 | 16.56 |

The results achieved for calcium oxalate RSS in dry foods (trial numbers 1–6) suggest that it is extremely difficult to modify the nutrient profile of dry dog foods to result in the production of a urine consistently undersaturated with calcium oxalate. However, the production of a urine with a calcium oxalate RSS of between 1 and 5 is well below the estimated formation product for calcium oxalate (RSS~10), above which spontaneous homogeneous crystallisation would be expected. Production of urine with calcium oxalate RSS<5 by normal healthy dogs carries a low risk of calcium oxalate formation. An interim nutrient profile has been formulated. Diets designed to this specification result in production of urine with a mean calcium oxalate RSS of less than 5 when fed to any canine animal, in particular to a small breed dog, predisposed to calcium oxalate formation (e.g. Miniature Schnauzer).

Struvite RSS

Although struvite formation tends to be linked to urinary tract infection in the majority of dogs, as a safety measure the diet should not put dogs at risk of struvite formation. The recommended struvite RSS should be less than 5.0.

Urine pH

These data suggest that a calcium oxalate RSS between 1 and 5 was more achievable if the means trial urine pH fell within the range of 5.5 and 6.0.

Example 4

Effect of Dietary Moisture Content on Urine Parameters of Miniature Schnauzers and Labrador Retrievers A study was conducted to assess the effect of dietary moisture content on urine parameters in miniature schnauzers (MS), (n=6) and Labrador retrievers (LR), (n=8). The dogs were divided into two groups and fed either a standard commercial dry dog food solus (8% moisture) or with added de-ionised water (75% moisture), for three week periods in a cross-over design.

Diet Nutrient Profile (g per 400 kcal)

| | |
|---|---|
| Moisture | 8.55 |
| Protein | 28.16 |
| Fat | 17.10 |
| Ash | 9.32 |
| Nitrogen free extract | 46.47 |
| Calcium | 1.78 |
| Phosphorus | 1.40 |
| Magnesium | 0.12 |
| Potassium | 0.70 |
| Sodium | 0.26 |

Urine was collected for measurement of urine volume, specific gravity and calcium oxalate RSS during each diet phase.

Figure 6:
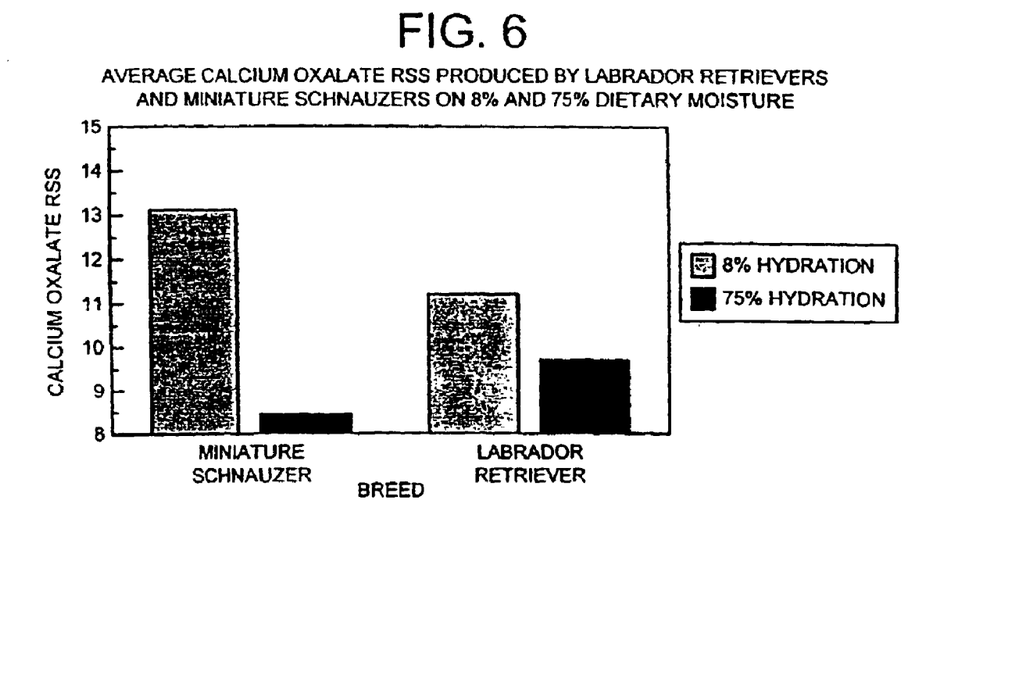
FIG. 6 is a graph showing average calcium oxalate RSS produced by certain dogs on 8% and 75% dietary moisture.
Figure 7:
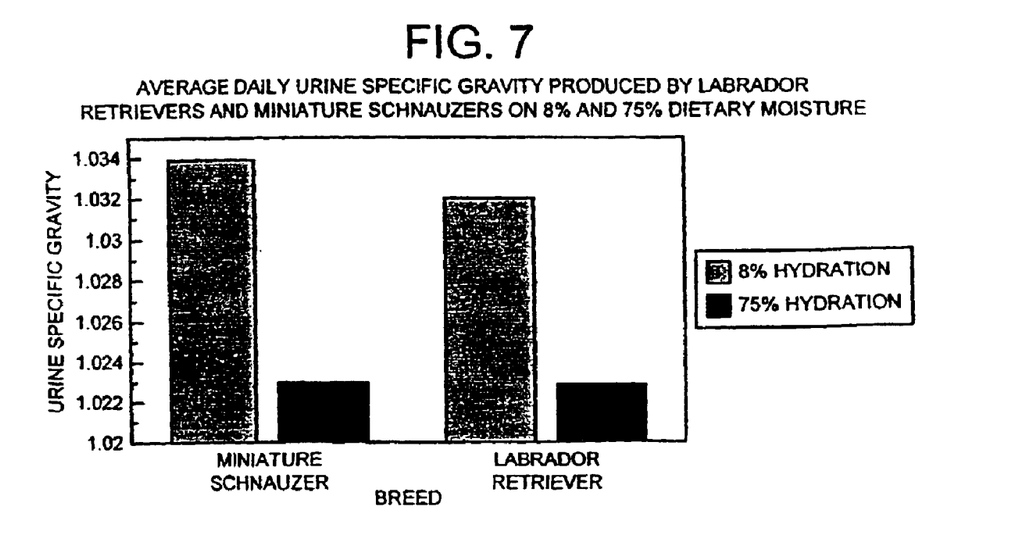
FIG. 7 is a graph showing average daily urine specific gravity producted by certain dogs on 8% and 75% dietary moisture.

When fed the dry food solus, the MS produced a calcium oxalate RSS close to the estimated formation product (RSS~14). Hydration of the food resulted in a significant decrease (p<0.05) in urinary calcium oxalate RSS (FIG. 6), and in specific gravity (FIG. 7). Hydration of the diet did not cause a significant change in urinary calcium oxalate RSS or urine specific gravity in the LR.

The results of this study showed that increasing dietary moisture content resulted in production of more dilute urine with a lower risk of calcium oxalate formation, in a breed of dog known to be susceptible to calcium oxalate urolithiasis.

Example 5

Effect of Dietary Sodium Content on Urine Parameters of Miniature Schnauzers and Labrador Retrievers A study was conducted to assess the effect of dietary sodium content on urine parameters in miniature schnauzers (MS), (n=4) and Labrador retrievers (LR), (n=7). The dogs were divided into two groups and fed either a standard commercial dry dog food solus (sodium content=0.2 g/400 kcal) or with added sodium chloride (total dietary sodium= 1.2 g/400 kcal), for three week periods in a cross-over design.

Diet Nutrient Profile (g per 400 kcal)

| Moisture | 6.32 |
| Protein | 29.62 |
| Fat | 14.31 |
| Ash | 8.76 |
| Nitrogen free extract | 51.91 |
| Calcium | 1.69 |
| Phosphorus | 1.15 |
| Magnesium | 0.09 |
| Potassium | 0.89 |
| Sodium | 0.23 |

Urine was collected for measurement of urine volume, specific gravity and calcium oxalate RSS during each diet phase.

Figure 8:
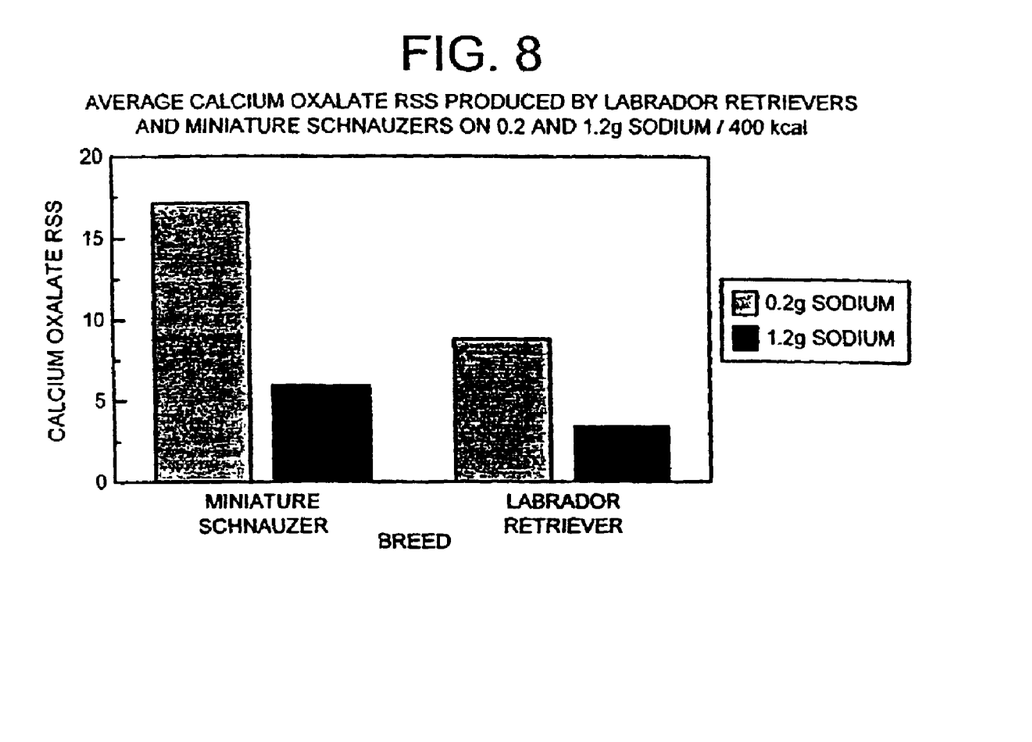
FIG. 8 is a graph showing average calcium oxalate RSS produced by certain dogs on 0.2 and 1.2 g Sodium/400 kcal.
Figure 9:
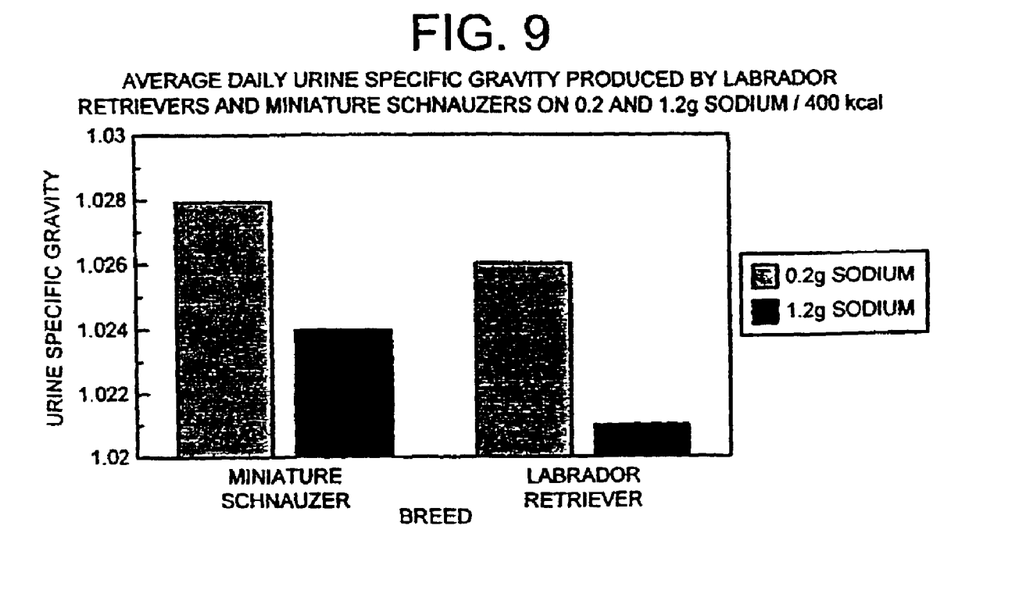
FIG. 9 is a graph showing daily specific gravity produced by certain dogs on 0.2 and 1.2 g Sodium/400 kcal.

When fed the dry food with low dietary sodium, the MS produced a calcium oxalate RSS around the estimated formation product (RSS~14). Supplementary dietary sodium resulted in a decrease in urinary calcium oxalate RSS (FIG. 8) and in specific gravity (FIG. 9). This effect was also produced by the LR, although the specific gravity and calcium oxalate RSS were not as high as the MS at any time.

The results of this study showed that increasing dietary sodium content resulted in production of more dilute urine with a lower risk of calcium oxalate formation, in a breed of dog known to be susceptible to calcium oxalate urolithiasis.

What is claimed is:

1. A comestible, comprising at least 0.04 g/400 kcal of magnesium, at least 0.5 g/400 kcal of potassium and the following ingredients in the ranges indicated, for use in preventing the initial occurrence of calcium oxalate urolithiasis in a canine animal:

| Nutrient | g/400 kcal |
|---|---|
| Calcium | 0.65–1.3 |
| Phosphorus | 0.5–1.2 |
| Sodium | 0.6–1.2. |

2. The comestible of claim 1 which when fed to a small breed canine animal results in a urine specific gravity of 1.025 or below.

3. A comestible, as claimed in claim 1 or claim 2, further comprising from 16 g/400 kcal of protein.

4. A comestible as claimed in claim 1 or 2, which has a moisture content of from 70% to 90%.

5. A comestible as claimed in claim 1 or 2, wherein the canine animal is a small breed dog.

6. A process for the preparation of a comestible as claimed in claim 1 or 2, comprising the steps of mixing together ingredients with optional cooking of any raw food ingredients and processing the mixture into a form suitable for consumption or administration to a canine animal.

7. The process, as claimed in claim 6, wherein the comestible comprises from 16 g/400 kcal of protein.

8. The process, as claimed in claim 6, wherein the comestible has a moisture content of from 70% to 90%.

9. The process, as claimed in claim 6, wherein the canine animal is a small breed dog.

10. A method of preventing the initial occurrence of calcium oxalate urolithiasis in a canine animal, comprising feeding to said canine animal a comestible comprising at least 0.04 g/400 kcal of magnesium, at least 0.5 g/400 kcal of potassium and the following ingredients in the ranges indicated:

| Nutrient | g/400 kcal |
|---|---|
| Calcium | 0.65–1.3 |
| Phosphorus | 0.5–1.2 |
| Sodium | 0.6–1.2. |

11. A method of preventing the initial occurrence of calcium oxalate urolithiasis in a small breed canine animal, comprising feeding to said canine animal the comestible of claim 1 which results in said canine animal having a urine specific gravity of 1.025 or below.

12. A method, as claimed in claim 7 or claim 8, wherein the comestible further comprises from 16 g/400 kcal protein.

13. A method, as claimed in claim 7 or 8, wherein the canine animal is a small breed dog.

14. A method, as claimed in claim 7 or 8, wherein the comestible has a moisture content of from 70 to 90%.

15. A method, as claimed in claim 7 or 8, which is fed to a canine animal for a period of from six weeks.

* * * * *